United States Patent
Munday et al.

(10) Patent No.: US 9,585,703 B2
(45) Date of Patent: Mar. 7, 2017

(54) INTRAMEDULLARY COMPRESSION SCREW SYSTEM

(71) Applicant: Agent Medical, LLC, Richmond, VA (US)

(72) Inventors: Jon Scott Munday, Richmond, VA (US); Earnest P. Sims Mawusi, Newport News, VA (US)

(73) Assignee: Agent Medical, LLC, Richmond, VA (US)

( * ) Notice: Subject to any disclaimer, the term of this patent is extended or adjusted under 35 U.S.C. 154(b) by 0 days.

(21) Appl. No.: 14/844,087

(22) Filed: Sep. 3, 2015

(65) Prior Publication Data

US 2016/0081727 A1    Mar. 24, 2016

Related U.S. Application Data (60) Provisional application No. 62/052,509, filed on Sep. 19, 2014.

(51) Int. Cl.
| | | |
|---|---|---|
| *A61B 17/72* | (2006.01) | |
| *A61B 17/86* | (2006.01) | |
| *A61B 17/68* | (2006.01) | |
| *A61B 17/16* | (2006.01) | |
| *A61B 17/88* | (2006.01) | |

(52) U.S. Cl.
CPC ...... *A61B 17/7225* (2013.01); *A61B 17/7291* (2013.01); *A61B 17/864* (2013.01); *A61B 17/164* (2013.01); *A61B 17/1615* (2013.01); *A61B 17/1686* (2013.01); *A61B 17/8875* (2013.01); *A61B 17/8883* (2013.01); *A61B 2017/681* (2013.01); *A61B 2090/061* (2016.02); *A61B 2090/062* (2016.02)

(58) Field of Classification Search
CPC ...................................... A61B 17/72–17/7291
USPC .................................................. 606/62–68
See application file for complete search history.

(56) References Cited

U.S. PATENT DOCUMENTS

| | | |
|---|---|---|
| 5,019,079 A | 5/1991 | Ross |
| 5,100,405 A | 3/1992 | McLaren |
| 5,217,462 A | 6/1993 | Asnis |
| 5,827,285 A | 10/1998 | Bramlet |
| 5,964,767 A | 10/1999 | Tapia |
| 6,048,344 A | 4/2000 | Schenk |
| 6,458,134 B1 | 10/2002 | Songer |
| 2006/0106390 A1 | 5/2006 | Jensen et al. |
| 2009/0112261 A1 | 4/2009 | Barry |

(Continued)

*Primary Examiner* — Nicholas Plionis (57) ABSTRACT

An intramedullary compression screw device and method including a cannulated compression screw and a cannulated proximal module for enabling the joining and alignment of two or more phalanges at the proper compression to facilitate healing in a patient. The cannulated compression screw includes a smooth body portion, an external threaded portion, and a low profile head. The cannulated proximal module includes external self-cutting threads and internal threads complementary with the external threads of the cannulated compression screw. Means are provided for driving the proximal module into a proximal phalanx and for securing the compression screw into the proximal module. A proximal module sizing template provides a means for determining the proper diameter of proximal module for insertion in the proximal phalanx. A depth gauge is provides a means for determining the proper length of cannulated compression screw for attachment to the proximal module.

10 Claims, 9 Drawing Sheets

(56) References Cited

U.S. PATENT DOCUMENTS

2011/0166602 A1 7/2011 Malek
2013/0226250 A1 8/2013 Rinner
2013/0304068 A1 11/2013 Larche et al.

INTRAMEDULLARY COMPRESSION SCREW SYSTEM

This application claims the priority of Provisional U.S. Patent Application Ser. No. 62/052,509 filed Sep. 19, 2014.

FIELD OF THE INVENTION

This invention relates to correction of misalignment, deformities, or fractures of interconnecting bones within the hand and foot and, more particularly, to an intramedullary compression screw device and method for fixation osteotomies, fractures and reconstruction of the phalanges of the lesser digits in the foot and hand.

BACKGROUND OF THE INVENTION

Hammer toe, a deformity of the proximal interphalangeal joint of the second, third, or fourth toe causing it to be permanently bent, in severe or longstanding cases, may require surgery.

Several devices are commonly used for the surgical correction of hammer toe. One such method consists of a single-piece correction device that is threaded on one end. One problem with the single-piece device is that it does not provide a means of adjusting the compression between the phalanges being joined, which can lead to improper healing of the phalanges. A second problem with the single-piece device is that it cannot be adjusted to correlate to the length of the patient's phalanges. Thus the distal end of the device is usually left extending from the distal end of the patient's distal phalanx. As a result, the patient's skin around the extending portion of the device cannot be closed by surgery, thereby creating a pathway for infection while the patient is convalescing and awaiting the surgically joined phalanges to heal.

Accordingly, what is needed is an apparatus and method for enabling a surgeon to correct a hammer toe deformity while creating proper compression between the proximal phalanx and the middle phalanx of the foot. The apparatus and method include a proper diameter to fit within the phalanges of the specific toe being operated on. The hammer toe apparatus and method further requires a means of properly gauging the length of the correction apparatus to enable it to be flush with the end of the distal phalanx.

BRIEF SUMMARY OF THE INVENTION

The present invention comprises an intramedullary compression screw device and method for fixation osteotomies, fractures, and reconstruction of the phalanges of the lesser digits in the foot and hand. The compression screw device includes a cannulated compression screw with and a cannulated proximal module which enable the drawing together and alignment of two or more bone fragments at the proper compression to facilitate healing in a patient. The cannulated compression screw includes a smooth body portion, an external threaded portion, and a low profile hex head that connects to a hex head screwdriver. The cannulated proximal module includes external self-cutting threads and internal threads complementary with the external threads of the cannulated compression screw. A first end on the proximal module includes a notch for engagement by a proximal driver and a second end with a plurality of thread cutting elements. The intramedullary compression screw device further includes a proximal module driver, a screwdriver/depth gauge/planer device, and a proximal module sizing template. The proximal module sizing template is used to determine the proper diameter of proximal module for insertion of the proximal module in the proximal phalanx. A depth gauge portion of the screwdriver/depth gauge/planer device is used to determine the proper length of cannulated compression screw for attachment to the proximal module.

The method for reconstructing the proximal, middle, and distal phalanges of the foot or hand includes selecting a proximal module of the proper diameter, selecting a cannulated compression screw of the proper length, placing a planar edge on the ends of the proximal and middle phalanges being joined, aligning the three phalanges, drilling a hole through the middle and distal phalanges with a drill bit of a predetermined length until the drill bit extends from the distal phalanx, determining the proper length of compression screw by measuring the extended length of the drill bit with the depth gauge, inserting the cannulated compression screw through the distal and middle phalanges, and screwing the proximal end of the compression screw into the proximal module until the three phalanges are joined together with the proper compression and the head of the screw is flush with the end of the distal phalanx.

OBJECTS AND ADVANTAGES

A first object of the current invention is to provide an intramedullary compression screw device and method for fixation osteotomies, fractures, and reconstruction of the phalanges of the lesser digits in the foot and hand.

A second object of the invention is to provide an intramedullary compression screw device and method that develops the proper compression between the various phalanges of the hand or foot to promote proper fusing of the joined phalanges.

A further object of the invention is to provide a means for accurately determining the proper size proximal module for creating proper endosteal purchase in a proximal phalanx.

Another object of the invention is to provide a means for determining the optimal length of compression screw for use in joining the proximal, middle, and distal phalanges of a hand or foot.

A further object of the invention is to provide a proximal module with self-cutting threads to rapidly form internal threads within a medullary canal.

A further object of the invention is to provide a proximal module driver for engaging a proximal module in order to drive it into a proximal phalanx.

A further object of the invention is to provide a device that combines a screwdriver function, depth gauge function, and a planer function into one device for properly determining the length of compression screw required, preparing the joint surfaces, and joining three phalanges of a hand or foot with a desired amount of compression.

BRIEF DESCRIPTION OF THE SEVERAL VIEWS OF THE DRAWING(S)

Reference is made herein to the accompanying drawings, which are not necessarily drawn to scale, and wherein.

DETAILED DESCRIPTION

The present invention comprises an intramedullary compression screw device and method for fixating osteotomies, fractures and reconstruction of the phalanges of the lesser digits in the foot and hand. The system is used for fractures and deformities in small bones and the small digits such as hammertoe deformity, claw toe deformity, mallet toe deformity, and other deformities of the foot and hand. Although the device and method described herein can be used with either the hand or foot, the specific examples shown herein will be with respect to correction of a hammer toe deformity of a phalanx of the foot. Please note that the terms "phalange" and "phalanx" as used herein are equivalent. The meaning of the term "planing" as used herein refers to using a plane or sharp cutting surface to remove thin layers from the surface.

Figure 11:
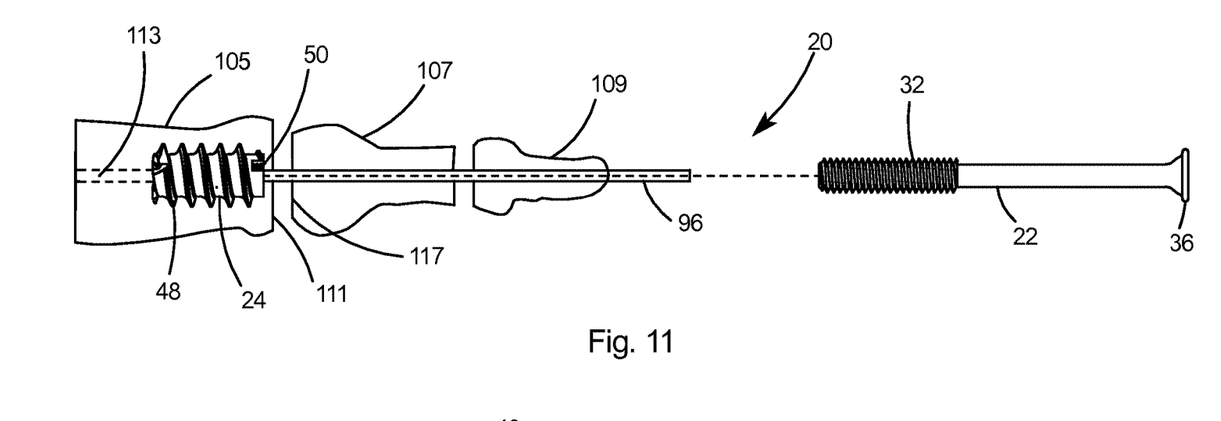
FIG. 11 is a side view of the compression screw and proximal module in alignment for correcting a hammer toe misalignment in accordance with embodiments of the invention.

With reference to FIG. 11, the two-piece intramedullary compression screw device 20 includes a cannulated compression screw 22 and a cannulated proximal module 24 which connect together to create the proper compression between the proximal phalanx and the middle phalanx of the foot in order to correct a hammer toe deformity.

Figure 1:
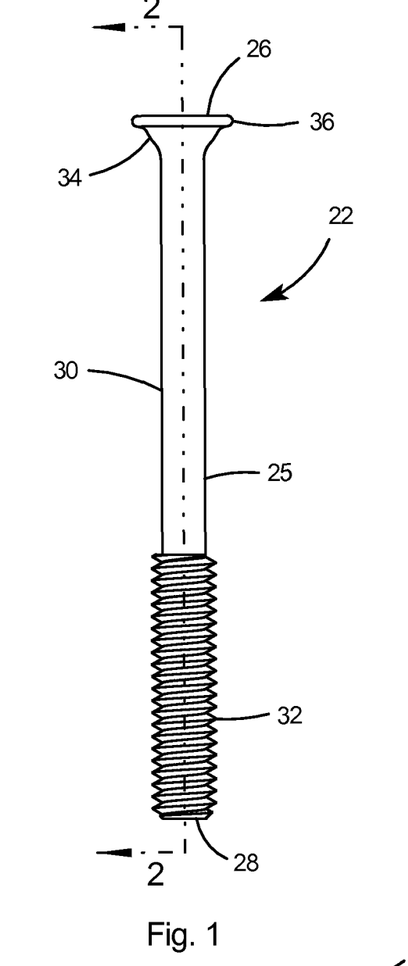
FIG. 1 is an elevation view of a compression screw in accordance with embodiments of the invention.
Figure 2:
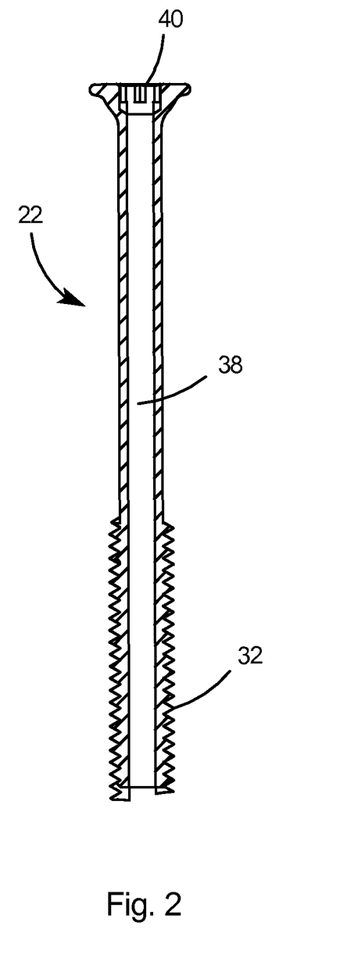
FIG. 2 is a sectional view of the compression screw taken along line 2-2 of FIG. 1.
Figure 3:
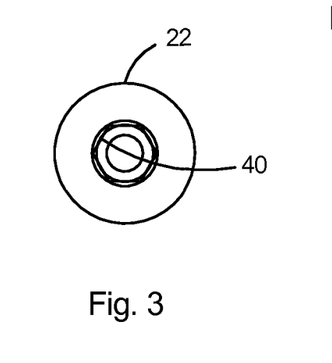
FIG. 3 is an end view of the compression screw as viewed from the top end of FIG. 1.

Referring to FIGS. 1-3, the cannulated compression screw 22 includes a body 25 having a first or distal end 26 and a second or proximal end 28, an unthreaded or smooth outer body portion 30 on the first end 26, and external threads 32 on the second end 28. Tapered shoulders 34 connect the smooth body portion 30 of the compression screw 22 to a low profile head 36, wherein low profile head as used herein indicates the length of the head as compared to the length of the compression screw is preferably a ratio of 0.06 or less. A bore 38 extends through the compression screw 22 and a hex surface 40 is provided within the head 36 as shown in FIG. 3.

The cannulated compression screw 22, the tapered shoulders 34, and the low profile head enable an easy insertion technique for reconstruction of the phalanges of the lesser digits in the foot and hand. The lengthy external threads provide for simple intra-operative sizing and the small diameter provides for reconstructive surgery of the second, third, and fourth phalanges of the lesser digits in the foot and hand.

Referring to FIG. 4-10, the cannulated proximal module 24 includes a body 42 including an inner or distal end 44 and an outer or proximal end 46. The proximal module body 42 includes self-cutting external threads 48 extending along the length of the body. A notch 50 is provided on the outer end 46 of the screw body. The proximal module 24 includes internal threads 52 that are complementary to the external threads 32 on the compression screw 22 (see FIG. 1).

Figure 4:
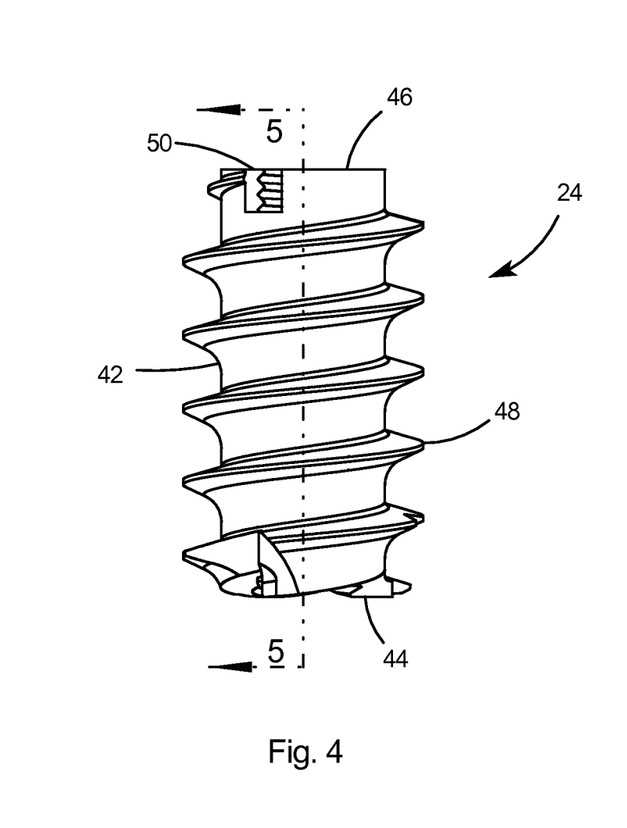
FIG. 4 is an elevation view of a proximal module in accordance with embodiments of the invention.
Figure 5:
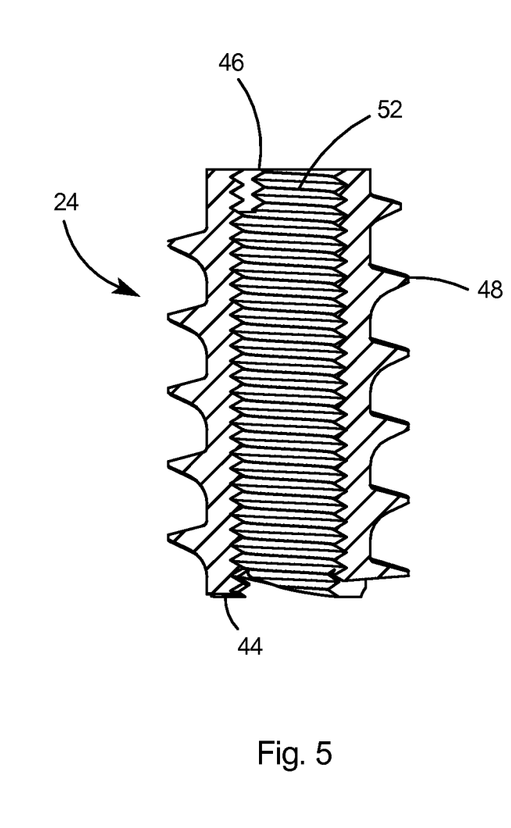
FIG. 5 is a sectional view of the proximal module taken along line 5-5 of FIG. 4.
Figure 6:
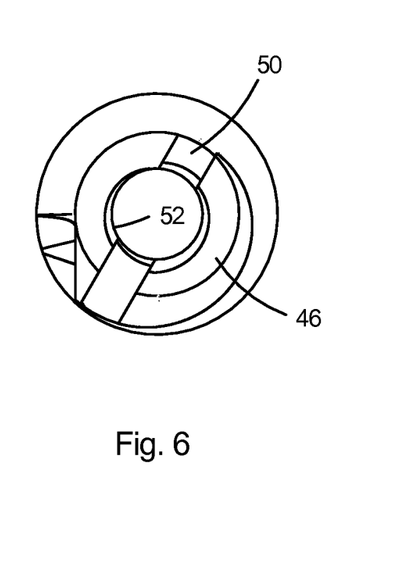
FIG. 6 is an end view of the proximal module as viewed from the top of FIG. 4.
Figure 7:
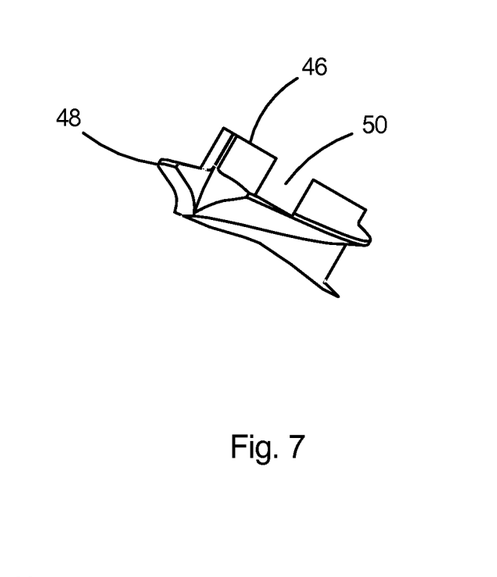
FIG. 7 is a side view of the end of the proximal module depicted in FIG. 6.
Figure 8:
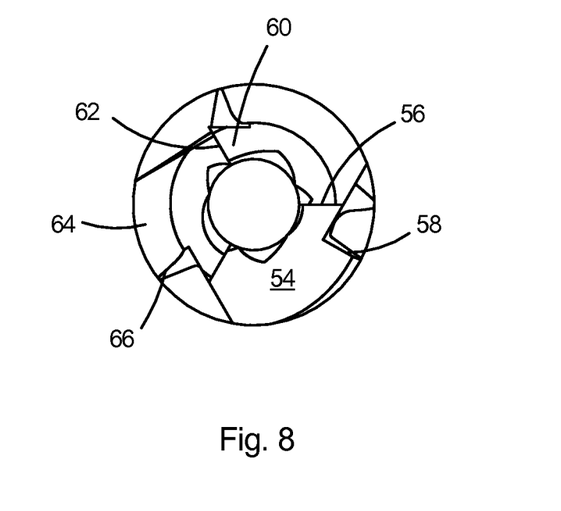
FIG. 8 is an end view of the proximal module as viewed from the bottom of FIG. 4.

The proximal module 24 is provided in three sizes, specified by its outer diameter, that are selectable by the surgeon for the specific diameter in order to surgically correct a deformity of the proximal interphalangeal joint of the second, third, or fourth finger or toe. Most preferably, the proximal module is provided in 4.0 mm, 4.5 mm, and 5.0 mm outer diameters to accommodate the various phalanges of the lesser digits in the foot and hand and differing anatomy of patients.

Figure 9:
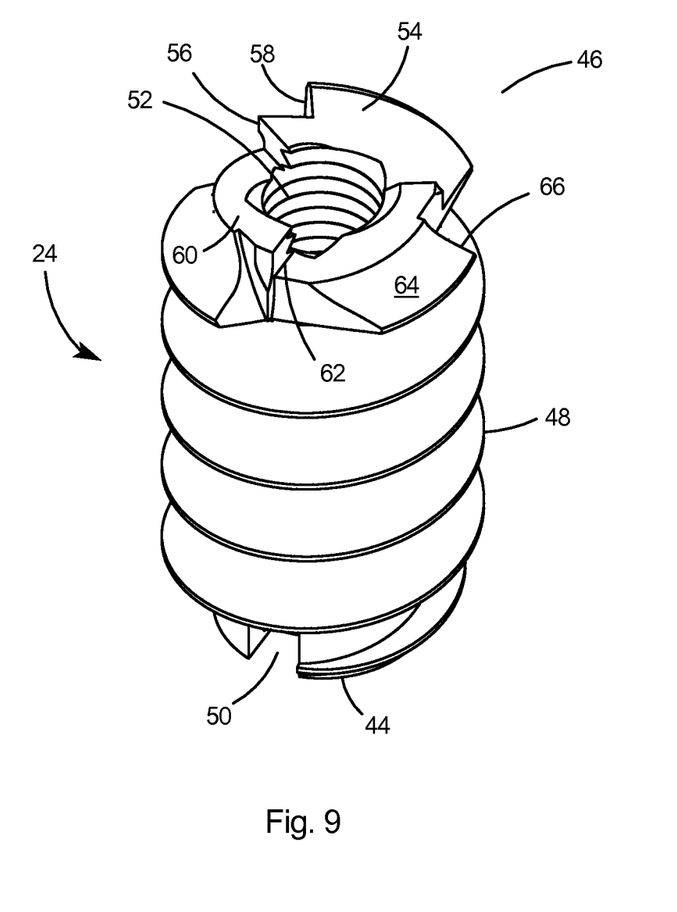
FIG. 9 is an isometric view of the proximal module as viewed from the distal end.
Figure 10:
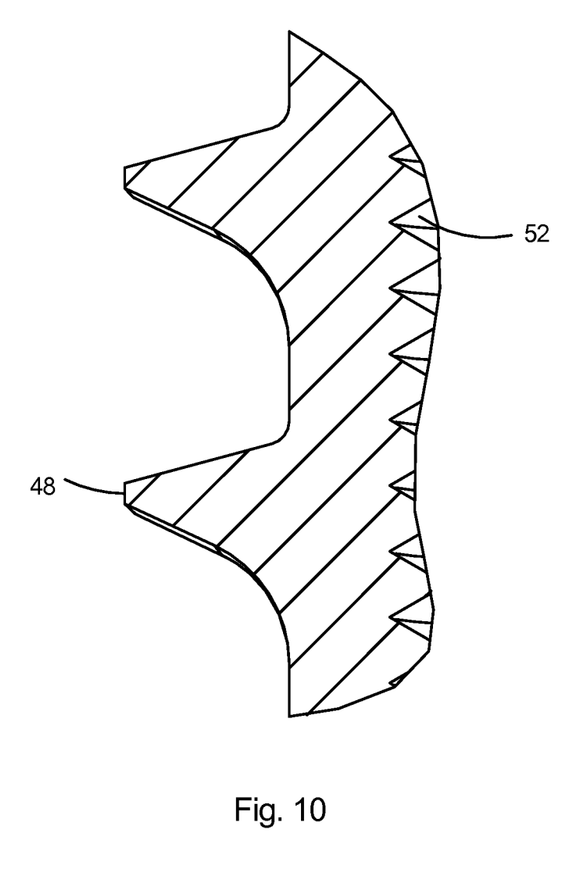
FIG. 10 is a sectional view of the proximal module taken along line 10-10 of FIG. 4.

With reference to FIG. 9, the self-cutting threads 48 of the proximal module 24 on the inner end 44 include a primary thread cutting element 54 including an inner cutting edge 56 and outer cutting edge 58 to initiate cutting of a thread as it is rotated within the medullary cavity of a bone. The self-cutting threads 48 further include a secondary thread cutting element 60 including a secondary cutting edge 62 and a tertiary cutting element 64 including a tertiary cutting edge 66. The self-cutting threads provide a simple, self-cutting insertion technique. The self-cutting external threads 48 provide generous endosteal purchase for component construct stability. The internal threads 52 accept the compression screw 22 for easy and secure assembly of the phalanges of the lesser digits in the foot and hand.

As described herein, the intramedullary compression screw system is a two-piece cannulated compression device 20 composed of 1) a threaded proximal module 24 (selectable from 4.0, 4.5 and 5.0 mm outer diameter sizes) that is secured within the proximal phalanx medullary canal, and 2) a cannulated screw 22 with low profile head 36 (selectable from lengths of 15, 20, 25, 30, 35, 40, 45, and 50 mm size) that is threaded into the previously inserted proximal module 24. The proximal module 24 is cannulated to fit over an insertion instrument and the compression screw 22 is cannulated to fit over a 0.035" K-wire for guided insertion of both components within the phalangeal digit medullary canal. The threaded advancement of the compression screw 22 within the stationary threaded proximal module 24 enables the creation of internal compression across the debrided digit joint space for stabilization and eventual fusion/arthrodesis, thereby resulting in pain relief, bone fixation, and joint deformity correction. Most preferably, the threaded proximal module 24 and compression screw 22 with low profile head are each manufactured in one-piece from high strength 6-4 ELI Titanium Alloy with an Anodized Type II surface.

Figure 14:
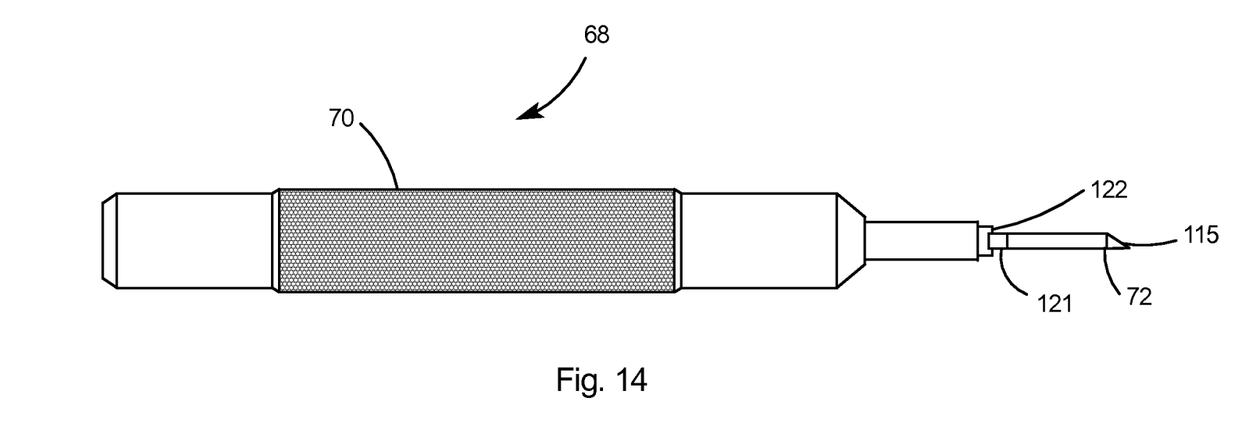
FIG. 14 is a side view of a proximal module driver in accordance with embodiments of the invention.
Figure 15:
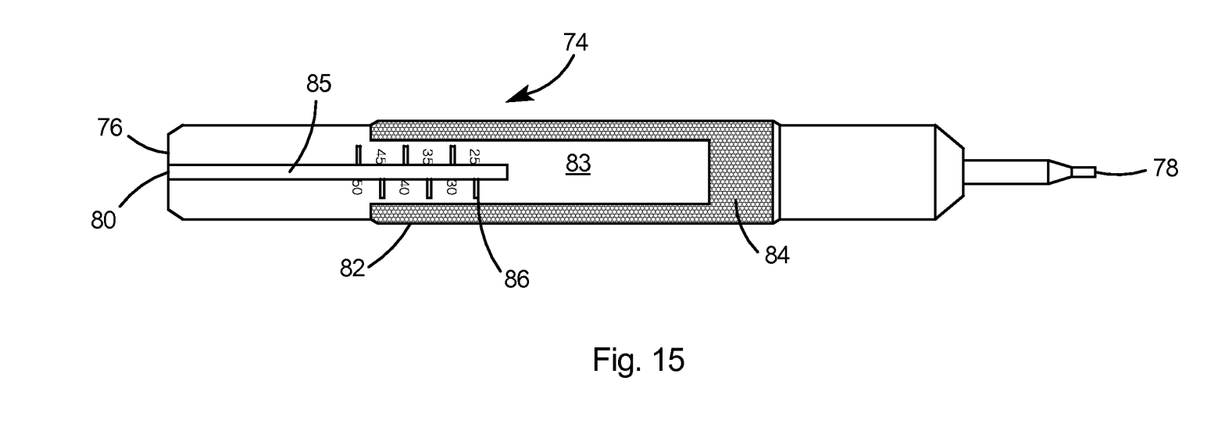
FIG. 15 is a side view of a screwdriver/depth gauge/planer in accordance with embodiments of the invention.

With reference to FIGS. 14 and 15, in accordance with further embodiments of the invention, the intramedullary compression screw system of the present invention may further include a proximal module driver 68 having a handle 70, an obturator end 72, and a screwdriver/depth gauge/planer device 74. The screwdriver/depth gauge/planer device 74 includes a planer end 76, a screwdriver end 78. The planer end 76 is cannulated, including a bore 80 extending into the proximal module driver from the planer end. A handle 82 including a hex surface 84 is provided on a substantial portion of the planer end. A portion of the handle 82 is smooth 83 and includes a groove 85 therein and indicia 86 in the proximity of the groove. The indicia 86 include marks to indicate a graduated scale for measuring the proper length of cannulated screw to use for a particular reconstructive surgery of the phalanges of the lesser digits in the foot and hand.

Figure 13:
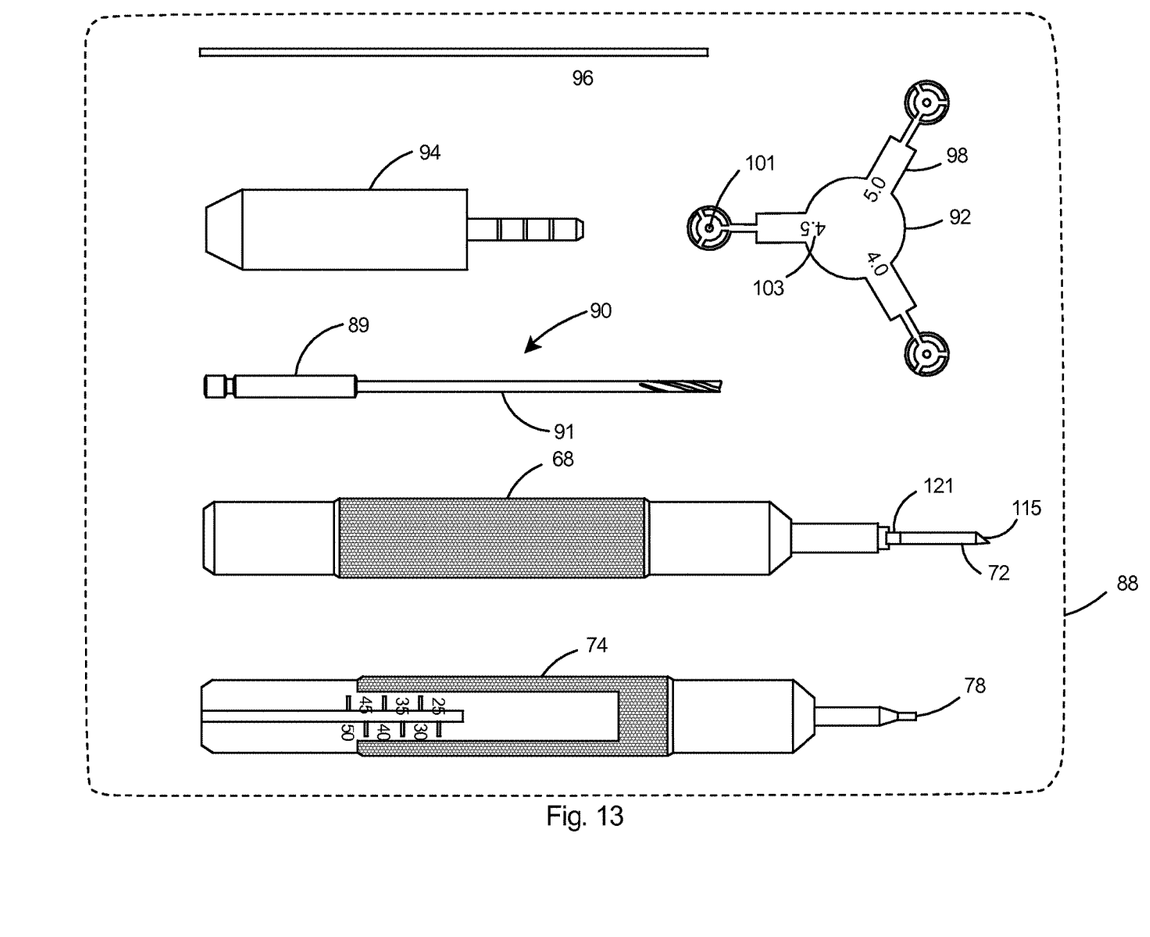
FIG. 13 is a plan view of a kit for correcting a hammer toe malalignment in accordance with embodiments of the invention.

With reference to FIG. 13, in accordance with further embodiments of the invention, the intramedullary compression screw system of the present invention may further include a disposable instrument kit 88 for use with the intramedullary compression screw device. The instrument kit 88 includes the proximal module driver 68, the screwdriver/depth gauge/planer device 74, a cannulated drill bit 90 having a hub 89 and a bit 91, a proximal module sizing template 92, a proximal module removal tool 94, and one or more guide wires 96. The proximal module sizing template 92 preferably includes one or more arms 98 with apertures 101 therein. Each of the arms 98 on the proximal module sizing template 92 includes indicia 103 to identify the diameter of the aperture 101 on that arm. The cannulated drill bit 90, guide wires 96, proximal module sizing template 92, and screwdriver/depth gauge/planer device 74 are preferably for single use. If necessary, removal of the compression screw device is accomplished percutaneously. All devices within the disposable instrument kit 88 are sterilized with ethylene oxide and packaged in sterile condition for single use.

The compression screw device of the present invention provides a method for fixation osteotomies, fractures and reconstruction of the phalanges of the lesser digits in the foot and hand. The method is used to draw two or more aligned bone fragments together at the proper compression to facilitate healing in a patient.

Figure 12:
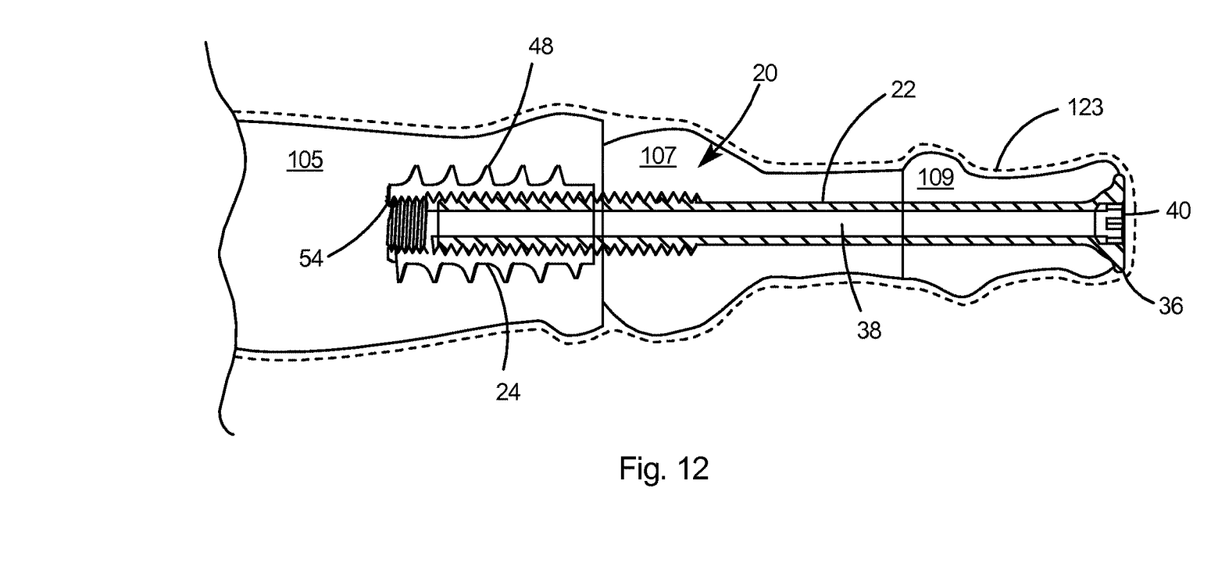
FIG. 12 is a sectional view of the compression screw and proximal module connected together to correct a hammer toe malalignment in accordance with embodiments of the invention.
Figure 16:
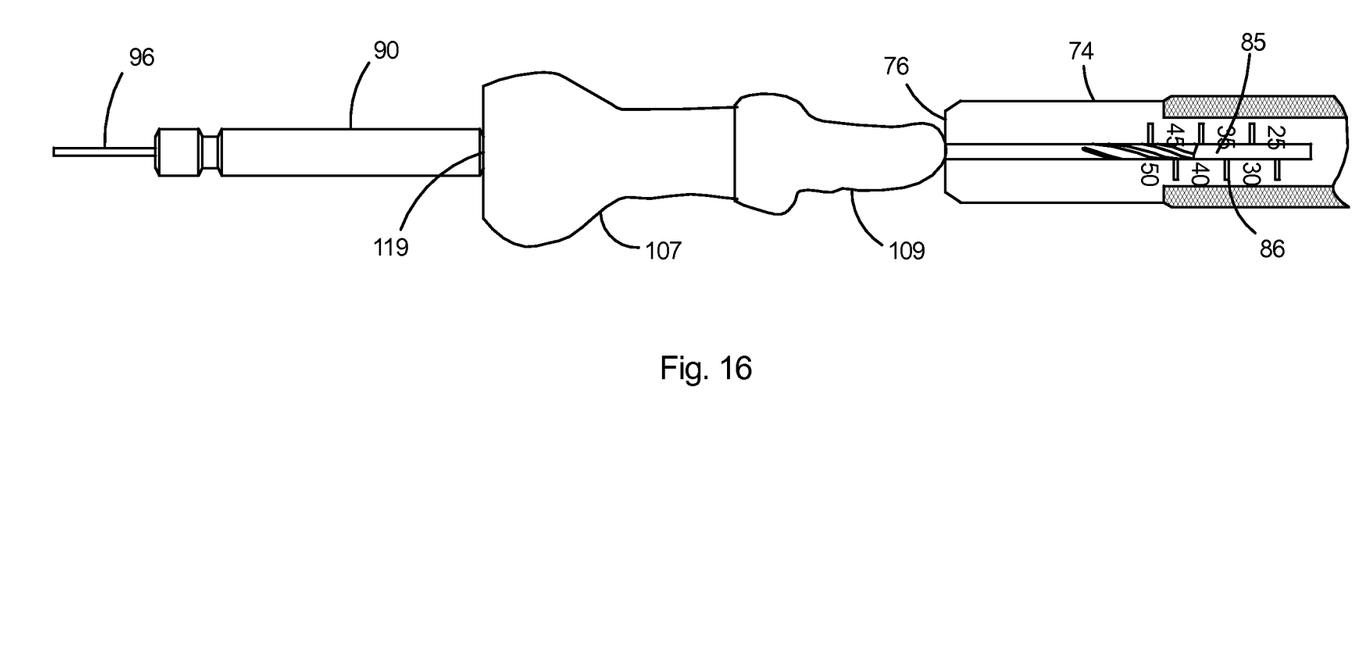
FIG. 16 is a side view depicting the procedure for using the screwdriver/depth gauge/planer device to determine the proper length of compression screw to be used in the surgical procedure.
Figure 17:
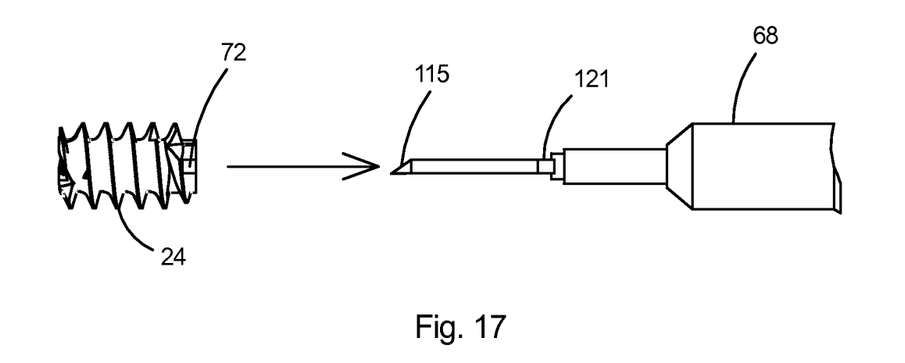
FIG. 17 is a side view depicting the obturator end of the proximal module drive in alignment with the proximal module.
Figure 18:
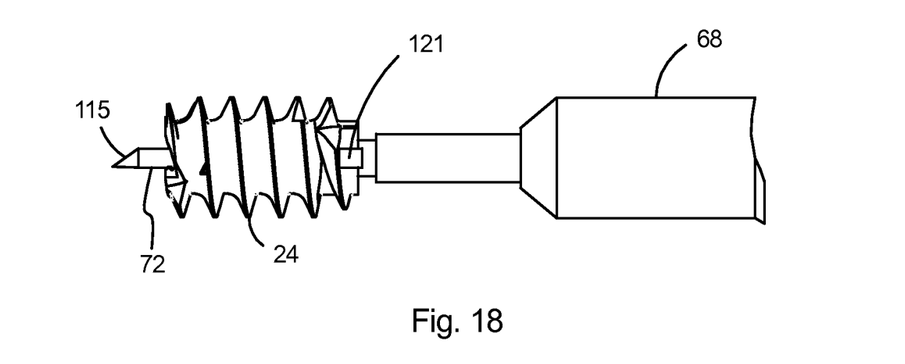
FIG. 18 is a side view depicting the obturator end of the proximal module drive in engagement with the proximal module.

With reference to FIGS. 11-12, a method for aligning and creating the proper compression between two or more bone fragments includes:
a) Exposing the surgical site by dissecting the skin to expose the joints of the proximal phalanx 105, middle phalanx 107, and distal phalanx 109.
b) Performing 1 mm-2 mm sub-articular osteotomies on the phalangeal surfaces of the proximal 105, middle 107, and distal 109 phalanges to create joint spaces there between.
c) Removing bone fragments and irrigating the joint spaces.
d) Determining the size of the proximal module 24 to be implanted into the distal end 111 of the proximal phalanx 105. Determining the size of the proximal module includes:
  i) Placing the proximal module sizing template 92 (see FIG. 13) against the end of the resected distal surface 111 of the proximal phalanx 105.
  ii) Selecting the correct size template (4.0 mm/4.5 mm/5.0 mm) that best covers the end of the resected surface of the bone without violating the peripheral cortex. The largest size of proximal module implant capable of filling the distal end of the proximal phalanx 105 within the cortex is chosen.
e) Locating the center of the proximal phalangeal bone canal 113 by inserting a guide wire 96, such as a 0.035" K-Wire (see FIG. 13) into the proximal phalanx 105.
f) Confirming the position of the guide wire 96 within the proximal phalanx 105 with fluoroscopy.
g) Removing the guide wire to create a pilot hole for guiding the obturator point 115 of the proximal module driver 68 (see FIG. 14) during proximal module 24 insertion.
h) Placing the self-cutting proximal module 24 over the obturator end 72 (see FIGS. 17 and 18) of the proximal module driver 68 so that the female notch 50 on the trailing end of the proximal module 24 lines up and fits onto the male flats 121 on the proximal module driver.
i) Inserting the obturator point 115 (see FIG. 15) of the proximal module driver 68 into the previously drilled hole in the end of the distal end 111 of the proximal phalanx 105.
j) Screwing the proximal module driver 68 with attached proximal module implant 24 clockwise into the end of the proximal phalanx 105 until the planer/platform 122 of the driver 68 touches the bone surface and, after cortical contact, planes the bone perpendicular to the proximal module implant 24 and recesses the implant 2 mm below the planed bone surface. The proximal module insertion depth into bone is dictated by the proximal module driver 68. The notches 50 of the proximal module 24 are fitted into male flats 121 on the proximal module driver 68 that are raised 2 mm from the surface of the planer 122. Therefore when the planer bottoms out on the bone the proximal module is placed exactly 2 mm below the surface of the bone. This is referred to as a 2 mm stage that the proximal module 24 sits on. The depth of proximal module insertion is therefore controlled by the proximal module driver 68 to a depth of 2 mm.
k) Driving the guide wire 96 retrograde through the middle phalanx 107, through the distal phalanx 109 and out the end of the digit. Fluoroscopy is used to confirm that the wire is within the confines of the medullary canals in all planes of the distal 109 and middle phalanges 107.
l) Inserting the planer end 76 of the screwdriver/depth gauge/planer device 74 over the proximal end of the guide wire 96 and the proximal surface 117 of the middle phalanx 107.
m) Planing the middle phalanx 107 flat by rotating the screwdriver/depth gauge/planer device 74 in both directions. The instrument is removed and the guide wire 96 is left in the bone throughout the remainder of the surgery.
n) Placing the cannulated drill bit 90 over the proximal end of the guide wire 96.
o) Drilling through the middle 107 and distal phalanges 109 with the cannulated drill bit 90. The drill bit is advanced until the hub of the drill bit is resting next to the proximal end 117 of the middle phalanx 107.
p) Placing the hub 119 of the cannulated drill bit 90 against the proximal surface 117 of the middle phalanx 107.
q) Placing the depth gauge 74 with the recessed groove 85 against the portion of the drill bit 90 extruding from the tip of the toe (see FIG. 16). The proper length of compression screw to be used is noted. If the tip of the drill bit lies between 2 markings, the longer measurement is used. This measurement takes into consideration the 2 mm recession of the proximal module 24 within the proximal phalanx 105 and the length of the proximal module 24 for screw coupling into the proximal module.
r) Making a small skin incision on either side of the guide wire 96 to accommodate the head of the cannulated compression screw 22 through the skin.

s) Extending the middle 107 and distal phalanges 109 in line with the proximal phalanx 105.
t) Extending proximal end of the guide wire 96 through the proximal module 24 to align the compression screw 22 with the proximal module 24.
u) Pushing the predetermined length compression screw 22 over the wire 96 and through the distal 109 and middle 107 phalanges until the tip of the screw 22 has exited the proximal end 117 of the middle phalanx 107 by approximately 2 mm.
v) Advancing the compression screw 22 by clockwise rotation of the screwdriver/depth gauge/planer tool 74 until the screw 22 is advanced through the proximal module 24 and all resected bone surfaces are in contact with each other and the head 36 of the screw 22 is flush with the end of the distal phalanx 109.
w) Removing the guide wire 96 from the joined intramedullary compression screw device 20.
x) Cleaning the surrounding area, preferably with a pulse lavage.
y) Closing the surgical site.

With reference to FIG. 12, after the surgical site is closed and the phalanges are given the requisite time to fuse together, the compression screw 22, including the low profile head 36 and the proximal module 24 remain within the digit. Unlike conventional single-piece compression devices, the two-piece intramedullary compression device of the present invention provides a means of adjusting the compression between the phalanges being joined, which leads to proper healing of the phalanges. As compared to single-piece compression devices, the two-piece intramedullary compression device 20 of the present invention further enables length adjustment to correlate the device to the patient's phalanges. The two-piece intramedullary compression device 20 furthermore does not leave the distal end of the device extending from the distal end of the patient's distal phalanx. As shown in FIG. 12, the skin 123 is closed by surgery, thereby eliminating any open pathway for infection.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. An intramedullary compression screw system for aligning and compressing the phalanges of the lesser digits in the foot or hand for healing, comprising:
    a cannulated compression screw including an unthreaded proximal end and an externally threaded distal end;
    a cannulated proximal module including a body having an open bore, internal threads and self-cutting external threads;
    a low profile hex head on said compression screw;
    a multi-edge cutting element on said self-cutting external threads;
    a proximal end and a distal end on said proximal module;
    said multi-edge cutting element including a plurality of thread-cutting elements on said distal end of said proximal module;
    said thread-cutting elements on said proximal module including a primary thread-cutting element, a secondary thread-cutting element, and a tertiary thread-cutting element; and
    an outer cutting edge and an inner cutting edge on said primary thread-cutting element of said proximal module, said inner cutting edge extending from said open bore of said proximal module partially through said proximal module body, said outer cutting edge extending from the outer surface partially through said proximal module body.

2. The compression screw system of claim 1, further comprising:
    a bore extending longitudinally through said compression screw; and
    a hex surface recessed in said low profile head of said compression screw.

3. The compression screw system of claim 1, further comprising:
    a notch on said proximal end of said proximal module, said notch extending through said body of said proximal module at said proximal end.

4. The compression screw system of claim 3, further comprising:
    a proximal module driver for engaging said proximal end of said proximal module;
    said proximal module driver including an obturator end and a planer platform surface;
    said proximal module driver including a male flat thereon for engaging said notch on said proximal module; and
    a rigid guide wire for aligning said phalanges.

5. The compression screw system of claim 1, further comprising:
    a secondary cutting edge on said secondary thread-cutting element; and
    a tertiary cutting edge on said tertiary thread-cutting element.

6. The compression screw system of claim 1, further comprising:
    a plurality of said proximal modules each having a unique diameter;
    a template for selecting the optimal diameter of proximal module for insertion in the proximal phalange; and
    a plurality of apertures in the template for facilitating selecting the optimal diameter of the proximal module.

7. The compression screw system of claim 6, wherein said plurality of proximal modules is selected from the group consisting of 4.0, 4.5 and 5.0 mm outer diameters.

8. The compression screw system of claim 1, further comprising:
    a screwdriver/depth gauge/planer device including a screwdriver end and a planer end; and
    a depth gauge including a groove extending from said planer end of said screwdriver/depth gauge/planer device; and
    said depth gauge including indicia adjacent said groove, wherein said indicia are at graduated distances from said planer end.

9. The compression screw system of claim 8, further comprising:
    a plurality of said compression screws, each of said compression screws having a unique length; and
    a drill bit including a hub and a bit, wherein the length of the compression screw is determined by extending said bit into said groove of said depth gauge until said hub contacts said planer end of said screwdriver/depth gauge/planer device.

10. The compression screw system of claim 9, wherein said plurality of compression screws are selected from the group consisting of 15, 20, 25, 30, 35, 40, 45, and 50 mm lengths.

* * * * *